United States Patent
Becker et al.

(10) Patent No.: US 10,010,443 B2
(45) Date of Patent: Jul. 3, 2018

(54) COUPLING FOR AN OSTOMY APPLIANCE

(75) Inventors: Kim Becker, Hillerød (DK); Kaspar Matthison-Hansen, Ålsgårde (DE); Troels Pedersen, Nivaa (DK)

(73) Assignee: Coloplast A/S, Humlebaek (DK)

( * ) Notice: Subject to any disclaimer, the term of this patent is extended or adjusted under 35 U.S.C. 154(b) by 877 days.

(21) Appl. No.: 14/127,494

(22) PCT Filed: Jun. 29, 2012

(86) PCT No.: PCT/DK2012/050230
§ 371 (c)(1),
(2), (4) Date: Nov. 10, 2014

(87) PCT Pub. No.: WO2013/004235
PCT Pub. Date: Jan. 10, 2013

(65) Prior Publication Data
US 2014/0324003 A1    Oct. 30, 2014

(30) Foreign Application Priority Data

Jul. 1, 2011  (DK) .................................. 2011 70353
Mar. 6, 2012  (DK) .................................. 2012 70102

(51) Int. Cl.
*A61F 5/448* (2006.01)
(52) U.S. Cl.
CPC ...... *A61F 5/448* (2013.01); *A61F 2005/4486* (2013.01)
(58) Field of Classification Search
CPC combination set(s) only.
See application file for complete search history.

(56) References Cited

U.S. PATENT DOCUMENTS

| | | | | |
|---|---|---|---|---|
| 2,796,063 A | * | 6/1957 | Smelser | A61F 5/448 604/342 |
| 3,833,497 A | * | 9/1974 | Belke | C25D 17/20 204/213 |
| 3,964,485 A | | 6/1976 | Neumeier | |
| 4,623,338 A | * | 11/1986 | Larson | A61F 5/4404 24/135 N |
| 4,664,661 A | * | 5/1987 | Ferguson | A61F 5/448 604/342 |
| 4,826,496 A | * | 5/1989 | Ferguson | A61F 5/448 604/339 |
| 4,917,691 A | * | 4/1990 | Briggs | A61F 5/448 604/339 |
| 4,929,245 A | * | 5/1990 | Holtermann | A61F 5/448 604/338 |

(Continued)

FOREIGN PATENT DOCUMENTS

| | | |
|---|---|---|
| CN | 1118134 | 9/1994 |
| WO | 9101118 | 2/1991 |

(Continued)

*Primary Examiner* — Todd J Scherbel
*Assistant Examiner* — Guy K Townsend
(74) *Attorney, Agent, or Firm* — Coloplast Corp., Coloplast A/S; Nick Baumann

(57) ABSTRACT

A coupling for an ostomy bag is provided. The coupling comprises a substantially non-extendable string functioning as locking ring in the coupling. The string is twisted by use of a tab when it is moved from an un-locked position to a locked position. A coupling as described can be made flexible and thereby more comfortable for the user.

20 Claims, 6 Drawing Sheets

(56) References Cited

U.S. PATENT DOCUMENTS

| | | | | |
|---|---|---|---|---|
| 5,026,360 A | * | 6/1991 | Johnsen | A61F 5/448 292/256.69 |
| 5,180,377 A | * | 1/1993 | Holtermann | A61F 5/448 604/338 |
| 5,322,522 A | * | 6/1994 | Olsen | A61F 5/448 604/332 |
| 5,364,379 A | * | 11/1994 | Ozenne | A61F 5/448 604/342 |
| 5,483,998 A | * | 1/1996 | Marelin | B25B 25/005 140/150 |
| 5,496,297 A | * | 3/1996 | Olsen | A61F 5/448 604/338 |
| 5,647,861 A | * | 7/1997 | Steer | A61F 5/448 215/279 |
| 5,902,295 A | * | 5/1999 | Steer | A61F 5/448 604/332 |
| 5,957,905 A | * | 9/1999 | Steer | A61F 5/448 604/338 |
| 2002/0165507 A1 | * | 11/2002 | Hessel | A61F 5/448 604/342 |
| 2009/0118687 A1 | * | 5/2009 | Kristensen | A61F 5/448 604/342 |
| 2014/0324003 A1 | * | 10/2014 | Becker | A61F 5/448 604/342 |
| 2015/0045755 A1 | * | 2/2015 | Pedersen | A61F 5/448 604/342 |

FOREIGN PATENT DOCUMENTS

| | | |
|---|---|---|
| WO | 9418919 | 9/1994 |
| WO | 0149225 | 7/2001 |
| WO | 0209629 | 2/2002 |

* cited by examiner

COUPLING FOR AN OSTOMY APPLIANCE

The invention relates to a mechanical coupling for an ostomy appliance wherein the locking ring comprises a string of substantially non-extendable material.

BACKGROUND

In connection with surgery for a number of diseases in the gastro-intestinal tract, one of the consequences in many cases is that the patient is left with an abdominal stoma, such as a colostomy or an ileostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time.

An ostomy appliance may be in the form of a two-piece appliance comprising a base plate and a collecting bag, which may be coupled to and un-coupled from each other through a coupling. This means that the base plate does not need to be separated from the skin of the user as often as exchange of the collecting bag requires. The base plate needs only be changed every third or fourth day depending on the user, whereas the collecting bag may be changed more than once per day.

DESCRIPTION OF RELATED ART

An example of a mechanical coupling can be seen from international publication no. WO91/01118, which discloses an ostomy coupling comprising a patient part with a neck and a bag part adapted to be coupled in tight-fitting relationship with the neck of the patient part. The coupling further comprises a locking ring for mutually retaining the two parts, which is elastically deformable and movably retained with respect to the patient part so that it is deformable between a first position and a second position, where the coupled parts are mutually loosely connected and mutually locked, respectively.

SUMMARY OF THE INVENTION

The invention relates to a coupling for an ostomy bag having a first and a second coupling, wherein one of the coupling members is adapted for being positioned on the wafer and the other is adapted for being positioned on the collecting bag. The second coupling member comprises an upstanding rib with a locking cam, which is adapted for cooperating with a notch on the first coupling member. In order to keep these two parts locked together in the coupled configuration of the coupling, a string is provided in a receiving channel below the two parts. Means for reducing the circumference of the string is provided and, therefore, the two parts are prevented from being removed from each other when the circumference of the string is reduced. When a string is used, a flexible coupling is achieved.

DETAILED DESCRIPTION OF THE INVENTION

In a first aspect, the invention relates to a coupling for an ostomy bag comprising
a first coupling member
a second coupling member
the first and second coupling members comprise cooperating coupling parts
the first coupling member comprising
a radially outwardly extending receiving channel
a locking ring in form of a substantially non-extendable string provided in the receiving channel, the locking ring being provided with means for reducing the circumference of the string so that the circumference can be reduced from a first un-locked position to a second locked position,
wherein the cooperating coupling parts are prevented from being released from each other when the string is in the second locked position.

By providing the locking ring of a string-material, a more flexible coupling is achieved, see results under Examples. The rigidity of a locking ring as described in the prior art is avoided. The substantially non-extendable material allows the string to provide the forces needed, which are radially inwardly directed forces to keep the locking cam of the second coupling member safely locked in the notch of the first coupling member to ensure a leak-proof connection between the parts.

In the following, whenever referring to the proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted to a user and the distal side is the opposite side—the side furthest away from the user when in use.

The axial direction is defined as the direction of the stoma, when the appliance is worn by a user. Thus, the axial direction is substantially perpendicular to the abdominal surface of the user.

The radial direction is defined as transverse to the axial direction, that is transversely to the direction of the stoma.

An ostomy appliance is well-known in the art. The collecting bag usually comprises a front wall on the distal side and a rear wall on the proximal side. The walls are made of gas- and liquid impermeable foil-material (for example of polyethylene (PE), polyvinyl-chloride (PVC) or ethylene-vinyl-acetate (EVA)) that is welded around the edges or the rim so as to form a pouch defining a waste collection chamber. The bag may be welded only partly around the rim so that an opening for emptying the bag is provided at the bottom of the bag. In that case the bag may be provided with means for closing that opening. The waste inlet opening is provided in the rear wall and placed in the upper part of the collecting bag so that when a user stands up, the waste inlet opening will be above the midline of the collecting bag. This leaves a larger collecting volume below the waste inlet opening. Thus, the top of the collecting bag is defined as the part closest to the waste inlet opening, and the bottom is defined as the opposite part.

The base plate usually comprises a skin-friendly adhesive on the proximal side.

The string may be made of a substantially non-extendable material. By substantially non-extendable is meant a string that will not become extended during the normal use as a locking ring. At least the string should not be able to extend so much that it can unintentionally move from the second locked configuration to the first unlocked configuration. In other words, the substantially non-extendable means that the extension of the string during normal use is less than 5%.

As an example it may be made of a fishing line such as "FireLine Fused Crystal" marketed by Berkley.

Another example is a polyester monofilament yarn such as type K380 from Monosuisse. This yarn has a density of 5300 dtex±265 dtex and a tenacity of 45 cN/tex±4.0 cN/tex. The tenacity provides a suitable non-extendable material.

The first coupling member includes a channel, which generally is U-shaped with the legs of the U extending radially out from the stoma when the appliance is fitted to the user. The string is at all times within the channel.

The first coupling member may be on the bag or on the wafer and the second coupling member on the other.

The first coupling member may be made of a relatively flexible material, for example low-density Polyethylene (LDPE). As an example of a suitable material, a material such as Exact® 0230, which is an ethylene based octene plastomer, may be used. This material has a flexural modulus of approximately 67 MPa, when measured according to ISO 178, which is contemplated to be a satisfactory level.

The second coupling member may be made of rigid material such as Polypropylene (PP).

The second coupling member may also be made from two components, for example in a two-shot injection moulding process. In this case a locking part may be made of a rigid material, for example PP, and an attachment part may be made of a flexible material, for example LDPE. The locking part then includes the locking cam adapted for cooperating with a notch in the first coupling member and the attachment part has a flange for welding the second coupling member to the wafer of the ostomy appliance. In this way the coupling will be a more flexible coupling when it is in the assembled or coupled position. As an example, the locking part may be made of a PP-material, Sabic® 58MNK 10, and the attachment part may be made of a LDPE material as the one described for use with the first coupling member. The PP material has a flexural modulus of approximately 1650 MPa, when measured according to ASTM D790, which is contemplated to be a satisfactory level for the locking part.

The cooperating coupling parts may comprise a notch on the first coupling member and a locking cam on the second coupling member, so that the locking cam is prevented from being released from the notch when the string is in the second locked position.

The coupling can be in a first uncoupled position and in a second coupled position—and intermediate positions there-between.

In a first uncoupled position of the coupling, the string of the locking ring is in its un-locked position and has a larger circumference than in the second coupled position of the coupling when the string is in its second locked position. The reduction in the circumference can be made in different ways.

In one embodiment, the reduction in circumference can be made by tying a knot providing the reduced circumference of the string. In another embodiment, the string is provided with a locking element that is able to keep the string in the locked position. As an example, a holder in form of a slider for shoelaces may be used as a locking element.

In another embodiment, the receiving channel of the first coupling member may be provided with a first and second level of surface, where the first level of surface has a first radial circumference greater than a second radial circumference of the second level of surface and the string is provided with a tab for holding the string in such a way that when the tab is twisted, the radial circumference of the string is shortened. In this embodiment, the tab functions as a locking element.

The embodiment described above has the advantage that when the string moves from one level of surface to the other, an audible indication such as a "click" can be heard by the user, whereby the user has a certainty that the locking ring is locked correctly.

In a first uncoupled position, the string of the locking ring is positioned at the first level of surface with the largest circumference and the string is in the first un-locked position. In the second coupled position, the string of the locking ring is in the second locked position and positioned at the second level of surface and the string is twisted so that its circumference is smaller than when it is un-twisted. The reduction in circumference preferably corresponds to the difference in circumference between the first level of surface and the second level of surface.

Between the first and second level of surface a slight protrusion may be present, the protrusion extending radially outwards so that this protrusion prevents the string from moving from the first level of surface to the second level of surface by itself.

The tab may be a substantially rectangular tab (in an example approximately 25 mm×20 mm) with a thickness of for example about 2 mm. The tab may be made of any type of rigid material, for example a polymeric material such as HDPE or PP. The string may be attached by threading it through a hole in the tab and tying a knot on the other side. Other types of attachment, such as gluing, welding, casting etc., may also be used. The distance between the attachment of the string and the corner of the tab should be large enough to prevent the tab from being twisted by itself. On the other hand, the distance should not be so large that it makes the tab too difficult to twist considering that when in use, the bag and the attachment flange on the first coupling member need to be pushed aside by the tab. A skilled person would know how to balance these two requirements.

In another embodiment, a locking element with a rotatable part, around which the string is threaded, is provided.

The rotatable part may be in form of a small wheel element around which the string is threaded.

The rotatable part may be in form of a tab pushing the string element to the side when an element is rotated.

In an embodiment, the string is crossed prior to being locked by a locking element so as to ensure that no part of the circumference of the coupling is untouched by the string.

Cross-laying of the string ensures that the coupling is tight all around the circumference of the coupling and prevents leaking at a non-overlayed point of the coupling.

However, overlaying or cross-laying of the string may for some types of strings lead to the fact that the string will seek to twist and unfold itself from the cross-laid position. Therefore another embodiment relates to a coupling including means for preventing twisting of a cross-laid string. The means for preventing twisting may be in form of a holding device on the locking element and/or ostomy bag. The holding device may be hooks and loops (e.g. Velcro®), buttons and button holes or snap fasteners. As an example, the locking element may be provided with one part of a snap fastener and the ostomy bag (e.g. the cover layer) may be provided with the matching part of a snap fastener. The holding device may also be provided as a slit in a cover layer for an ostomy bag where the locking element can be entered into a holding position.

An interesting embodiment is the use of an extra support ring having a circumference larger than the reduced circumference of the string. This support ring has the effect of holding the string in place, so that the string is prevented from twisting.

This extra support ring may be of a material that is more flexible than the locking element. As an example the support ring may be provided in a thermoplastic material such as PE. The support ring may be rather thin, for example about 1 mm×1 mm in cross-section.

In another embodiment, the string is wrapped twice around the coupling and then tied with a knot or held together by a locking element. Then it is always ensured that the string is in contact with the entire circumference of the coupling. At the same time the problems of the need for securing overlaying at the locking element or knot tying part are alleviated.

In a second aspect, the invention relates to a method of attaching an ostomy bag comprising a coupling with a first coupling member including a notch adapted for receiving a locking cam of a second coupling member, the first coupling member further comprising a receiving channel having a first and second level of surface and a locking ring in form of a substantially non-extendable string received therein, wherein the method comprising the steps of attaching a wafer including the second coupling member to the user positioning a collecting bag including the first coupling member on the wafer and pushing the locking cam of the second coupling member into the notch of the first coupling member reducing the circumference of the string in the receiving channel In an embodiment of the invention according to the second aspect, the reduction of the circumference is done by twisting on the string, for example when the string is attached to a tab as described above.

DETAILED DESCRIPTION OF THE DRAWING

Figure 1:
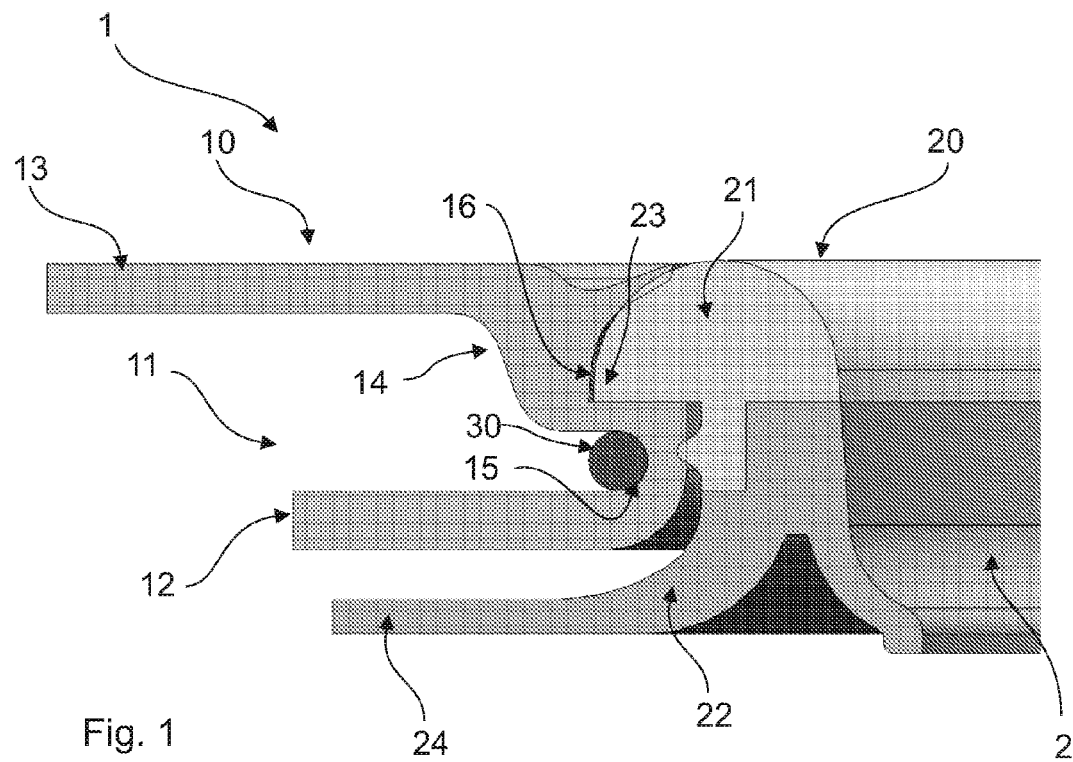
FIG. 1 illustrates a cross sectional view of a coupling according to the invention, the coupling is shown in a coupled configuration.

FIG. 1 illustrates a cross sectional view of a coupling 1 according to the invention. The coupling has a first coupling member 10 and a second coupling member 20. The first coupling member 10 may be welded to the ostomy bag and the second coupling member 20 may be welded to the wafer.

The first coupling member 10 is provided with a receiving channel 11 extending radially outwards from the inner periphery 2 of the coupling. The first coupling member further has flanges; a flange 12 adapted for containing the locking ring in the coupled position of the coupling and a flange 13 adapted for being welded to the collecting bag (not shown). These two flanges form the legs of the receiving channel.

The receiving channel 11 has two levels of surfaces, a first level of surface 14 with a greater circumference than a second level of surface 15.

The second coupling member 20 comprises in the shown embodiment a locking part 21 of a relatively rigid material and an attachment part 22 of a more flexible material. The locking part 21 includes the locking cam 23 and providing this part of a more rigid material helps prevent unintentionally uncoupling of the coupling parts. The flexible attachment part 22 includes a flange 24 adapted for being welded to the wafer of an ostomy appliance. By providing a part of the second coupling member of a more flexible material, the coupling will overall be more flexible and thus more comfortable for the user. However, the second coupling may be made entirely of a relatively rigid material.

In a first uncoupled position of the coupling, the locking ring 30 will be positioned at the first level of surface 14. In this position, the first coupling member 10 may be released from the second coupling member 20. In the position shown in FIG. 1, the coupling parts 10, 20 are illustrated in the coupled position and the locking ring 30 is positioned at the second level of surface 15. The locking cam 23 of the second coupling member 20 is positioned in a notch 16 of the first coupling member. In this position, the cooperation between the locking ring at the first coupling member and the locking cam at the second coupling member prevents the two parts from being uncoupled. Furthermore, the flexible material at the notch 16 provides a sealing effect between the two coupling parts so as to prevent output from the stoma from travelling through the coupling.

FIGS. 2 to 7 illustrate the locking ring 30 and how it functions when it is to be locked.

Figure 2:
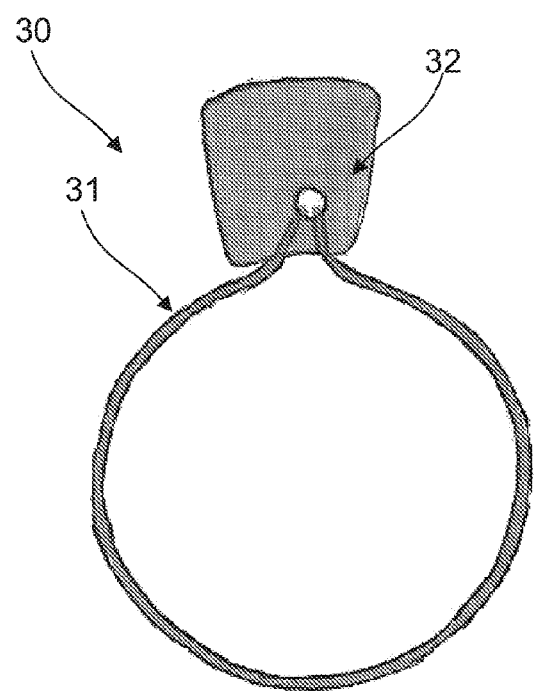
FIGS. 2 to 7 illustrate how the locking ring behaves when going from the un-twisted configuration to the twisted configuration.
Figure 3:
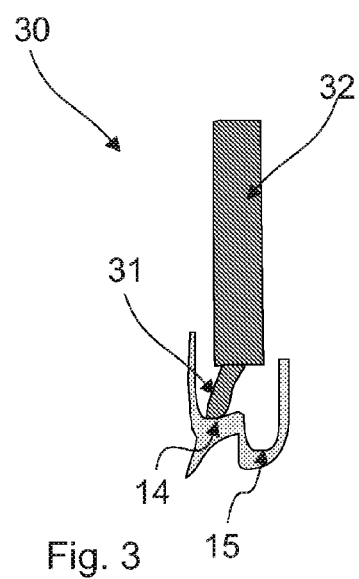

In FIG. 2 the locking ring 30 is illustrated in the un-locked position. The figure shows a front view of the locking ring. FIG. 3 shows a side-view and illustrates the position of the un-locked locking ring 30 at the first level of surface 14 in the first coupling member. FIG. 2 shows the string 31 of the locking ring 30 and that it is attached to a tab 32. The string 31 is un-twisted so it has the longest possible circumference.

Figure 4:
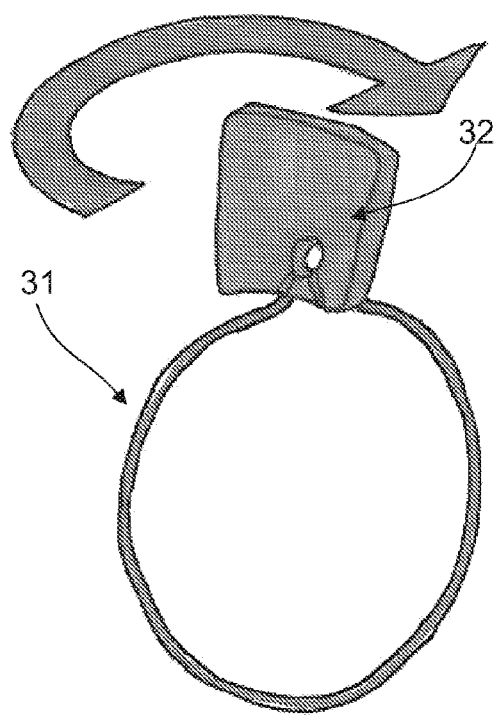
Figure 5:
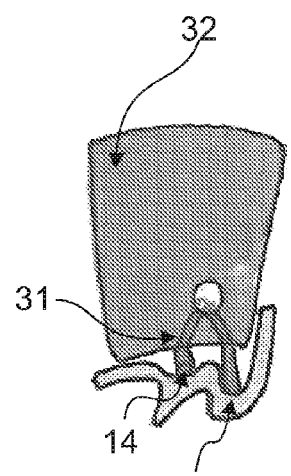
Figure 6:
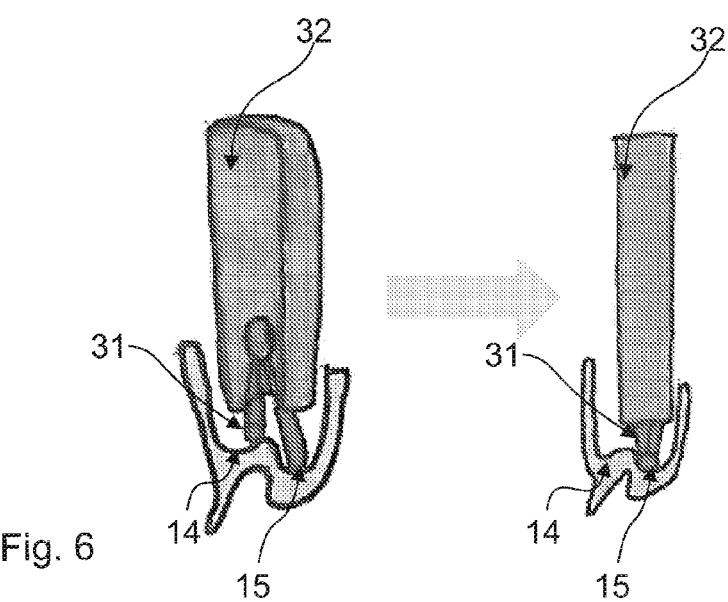

FIGS. 4 to 6 show side-views and illustrate how the twisting of the tab 32 moves the string 31 from the first level of surface 14 to the second level of surface 15. In the intermediate position prior to the tab being twisted 180 degrees, the string may be positioned partly on the first and partly on the second level of surface, which is schematically illustrated in the figures.

Figure 7:
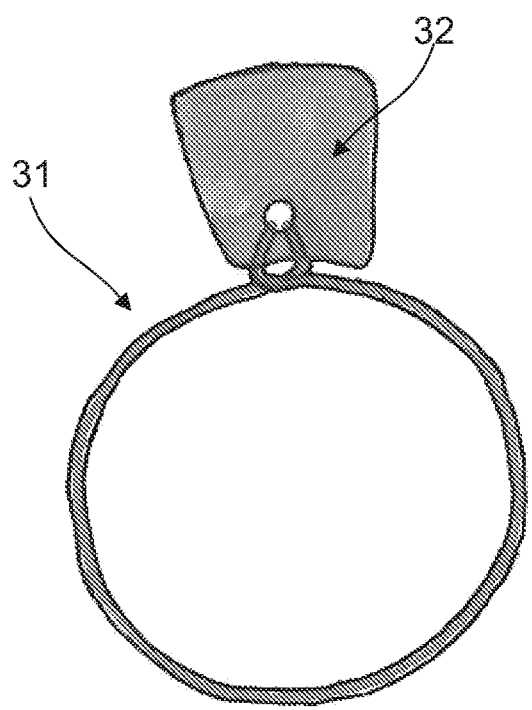

FIG. 7 illustrates a front view of the fully twisted string 31 and tab 32.

Figure 8:
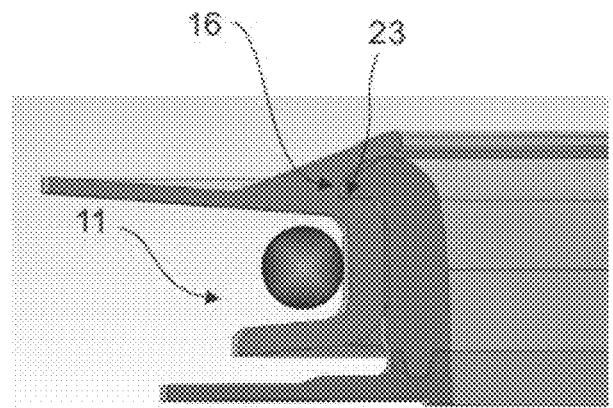
FIGS. 8-10 illustrate other embodiments of a coupling according to the invention

FIG. 8 illustrates another embodiment of a coupling according to the invention. In this embodiment, the receiving channel 11' has only one level of surface 14' and the coupling ring 30 keeps the notch 16 and the locking cam 23 in attachment with each other so that the first and second coupling part 10, 20 are prevented from being released from each other.

Figure 9:
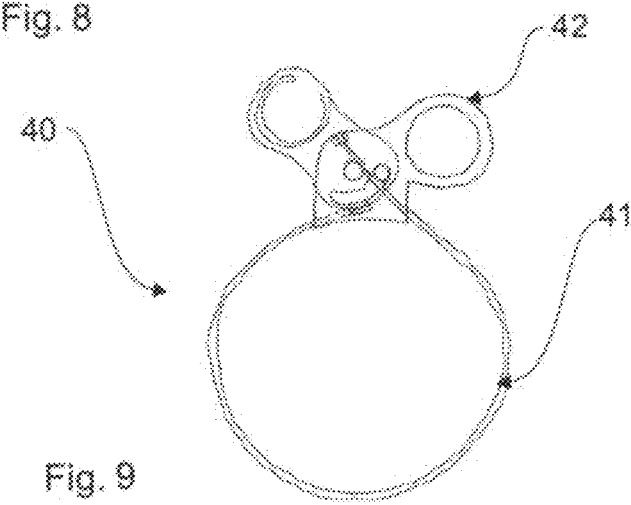

FIG. 9 illustrates an alternative locking ring 40 having a string-element 41 which is cross-laid as illustrated at 41a. In this embodiment, the tab is replaced by a rotating locking element 42 that upon rotation will shorten the string-element 41 by rotating the end around the element 42.

Figure 10:
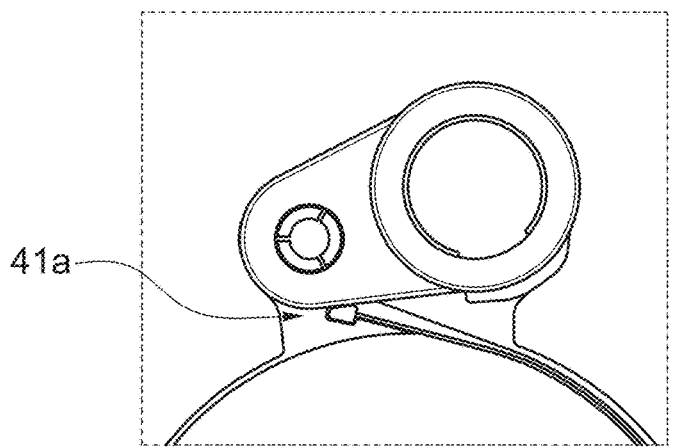

FIG. 10 illustrates the detail of how the locking element 42 can be provided with a snap-lock 43 so as to keep the locking ring in the locked or closed position.

Figure 11:
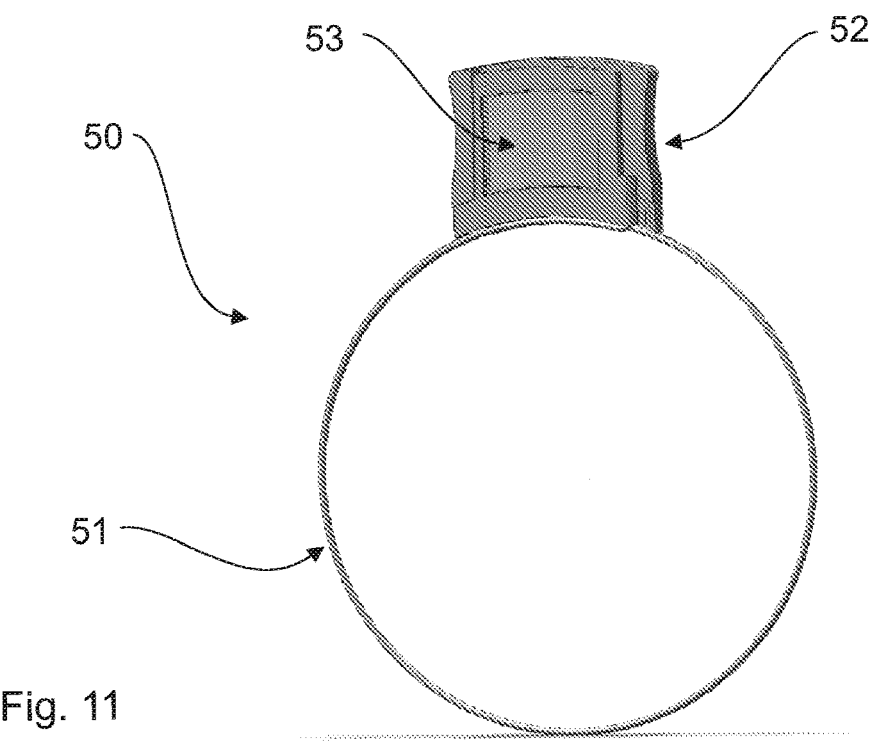
FIG. 11 illustrates an embodiment of a locking ring according to the invention

FIG. 11 illustrates another embodiment of a locking ring 50 according to the invention. This locking ring 50 is provided with a string element 51 that is attached to a locking element 52. The locking element 52 uses a snap mechanism 53 to keep the element in a locked position.

Figure 12:
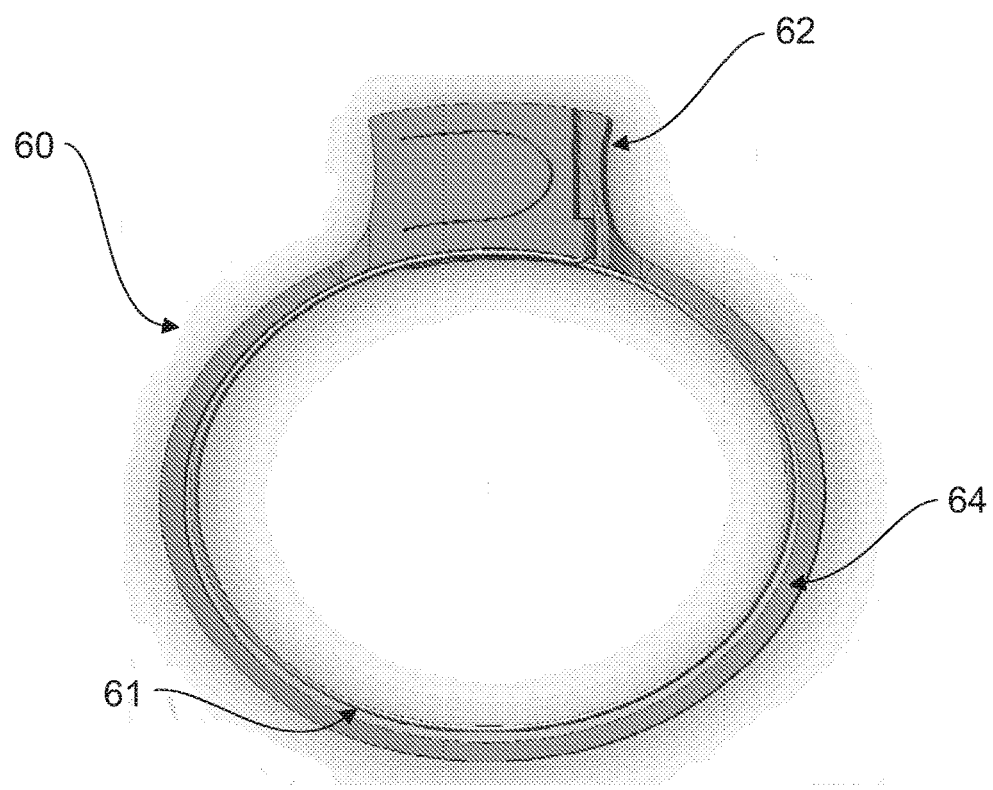
FIG. 12 illustrates another embodiment of a locking ring according to the invention

FIG. 12 illustrates an embodiment of a locking ring 60 which is very similar to the embodiment of FIG. 11. The locking element 62 used for locking the string element 61 is the same as in the embodiment of FIG. 11. The embodiment of FIG. 12 differs from the embodiment of FIG. 11 in that the embodiment of FIG. 12 is provided with a support ring 64. The support ring 64 assists in holding the string in place within the receiving channel at the coupling and further prevents the locking element 62 from twisting when the coupling is in use.

Example—Testing of Flexibility

The flexibility of a coupling with a substantially non-extendable string was tested. The coupling is as shown in FIG. 10.

Figure 13:
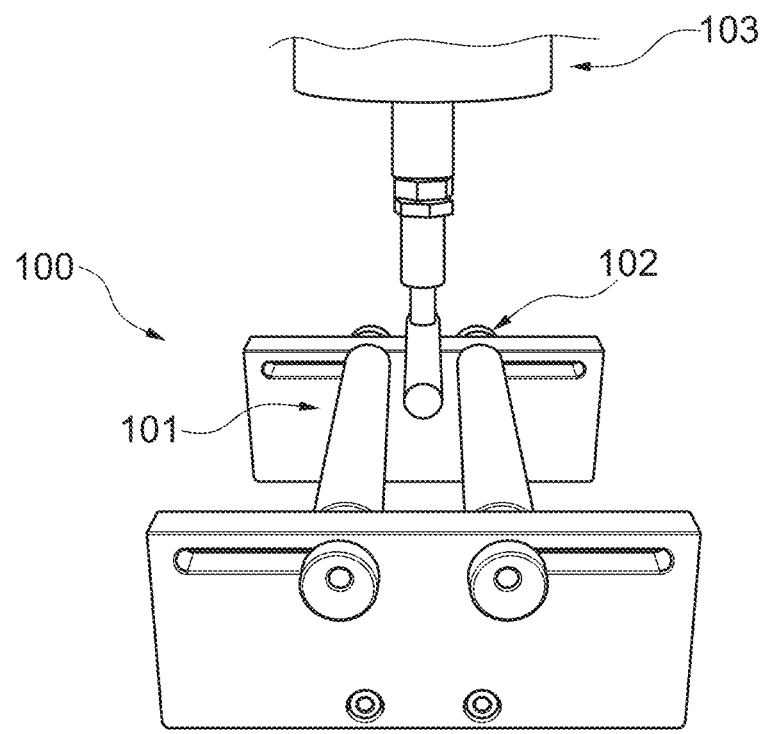
FIG. 13 illustrates a test-setup used to measure the flexibility of a coupling

The testing was performed in a standard three-point bending test-setup as shown in FIG. 13. The machine used was a regular instron testing machine (not shown) applying the bending at a rate of 30 mm/min. The test stops when the bending has reached 10 mm. The supports for the three-point bending test consist of two rollers 101 and the force is applied by a third roller 102 connected to a load cell 103.

A test specimen consists of a two-piece ostomy bag. Initially the release-liner was removed from the base plate (wafer). Then the base plate was mounted centrally on the rolls 101 and a collecting bag was attached to the base plate and locked using a locking ring.

The load used to bend the specimen 10 mm was measured.

Figure 14:
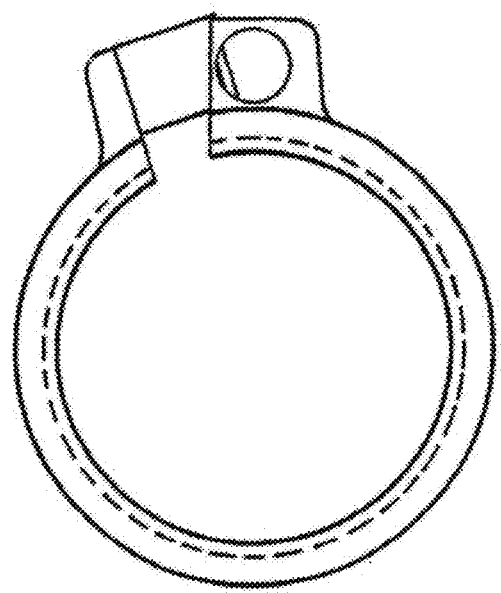
FIG. 14 illustrates a reference locking ring used for comparison tests of flexibility and compression testing.

For comparison, an ostomy bag with a coupling with a regular locking ring (as shown in FIG. 14 and described in WO91/01118) was tested in the same way. Furthermore, an ostomy bag without a locking ring was tested.

The results are shown in Table 1 below.

TABLE 1

| Test specimen | Stress |
| --- | --- |
| string-element | 6.63 N/mm |
| regular locking ring | 10.83 N/mm |
| without locking ring | 4.75 N/mm |

From the table above it appears that the string element coupling is much more flexible than the regular locking ring although it is less flexible than a coupling without a locking ring. However, a coupling without a locking ring is less secure than a coupling with a locking ring.

Example—Compression Testing

The ability to withstand compression was also tested.

An ostomy bag with a coupling with a locking ring in form of a string-element (as shown in FIG. 8) was tested by filling it with air and submerging it in water. The pressure inside the bag was measured. The highest pressure was noted inside the bag when bubbles occurred, the bubbles indicate a leakage in the ostomy bag. For comparison, an ostomy bag with a coupling with a regular locking ring (shown in FIG. 14 and described in WO9101118) was tested the same way. The locking ring is marketed by Coloplast A/S on the product Assura® Click.

The results are shown in Table 2 below.

TABLE 2

| Test specimen | Pressure inside bag |
| --- | --- |
| String-element | 101 mBar |
| regular locking ring | 76 mBar |

From the table above it appears that the string element coupling is able to withstand a higher pressure than the regular locking ring.

The invention claimed is:

1. A coupling assembly for an ostomy appliance, the coupling assembly comprising:
    a first coupling member including a first flange that is attachable to an ostomy bag of the ostomy appliance, a second flange spaced apart from the first flange by a channel, a release surface located in the channel between the first flange and the second flange, and a lock surface located in the channel between the release surface and the second flange;
    a second coupling member including an inner periphery part, an attachment part connected to the inner periphery part, a wafer flange connected to the attachment part and configured to be attached to a wafer of the ostomy appliance, and a locking cam connected to the attachment part;
    a locking ring located in the channel of the first coupling member, where the locking ring has a first end portion and a second end portion; and
    a locking element attached to the locking ring, the locking element configured to move the locking ring reversibly between the lock surface and the release surface;
    wherein, when the locking ring is engaged with the lock surface, the first end portion crosses-over and extends circumferentially beyond the second end portion, the second end portion engages with the lock surface such that the locking ring is in contact with an entire circumference of the channel, the locking cam of the second coupling member is engaged with the first coupling member to prevent uncoupling of the first coupling member from the second coupling member;
    wherein the locking element connects to the first end portion as it extends circumferentially beyond the second end portion, the locking element configured to move the first end portion between the lock surface and the release surface;
    wherein, when the locking ring is engaged with the release surface, the locking cam of the second coupling member is disengaged from the first coupling member to allow the first coupling member to be uncoupled from the second coupling member.

2. The coupling assembly of claim 1, wherein the first flange of the first coupling member is parallel to the second flange of the first coupling member.

3. The coupling assembly of claim 1, wherein the first flange of the first coupling member defines an outer perimeter of the first coupling member, and the lock surface is located farther away from the outer perimeter of the first coupling member than the release surface is located from the outer perimeter of the first coupling member.

4. The coupling assembly of claim 1, wherein the channel defines an interior of the first coupling member and the first coupling member further comprises a notch located opposite of the channel on an exterior of the first coupling member, with the notch sized to receive and engage with the locking cam of the second coupling member.

5. The coupling assembly of claim 1, wherein the locking element includes a tab attached to the locking ring, the tab configured to move the locking ring reversibly between the lock surface and the release surface.

6. The coupling assembly of claim 1, wherein the locking ring is a string and the locking element is a slider attached in sliding engagement with the string.

7. The coupling assembly of claim 1, wherein the locking ring is a string and the locking element is a tab, with the string oriented in a circular configuration having a first circumference.

8. The coupling assembly of claim 7, wherein rotation of the tab twists the string into a second circumference that is less than the first circumference.

9. The coupling assembly of claim 1, wherein the first coupling member is an annular coupling member providing the release surface with an annular release surface circumference that is larger than an annular lock surface circumference of the lock surface.

10. The coupling assembly of claim 9, wherein the locking ring is a string having a string circumference sized to encircle the annular release surface, and the locking element is a tab such that twisting the tab reduces the string circumference to the annular lock surface circumference.

11. The coupling assembly of claim 1, wherein the locking ring is a monofilament yarn that is permanently located in the channel.

12. The coupling assembly of claim 1, wherein the locking cam has a cam surface that extends a cam length in a radial direction away from the attachment part, with the cam surface parallel to the wafer flange, and the circle diameter of the locking ring is smaller than the cam length of the cam surface of the locking cam.

13. The coupling assembly of claim 1, wherein the locking ring is in contact with an entire circumference of the release surface of the channel.

14. The coupling assembly of claim 1, wherein the locking ring is in contact with an entire circumference of the lock surface of the channel.

15. The coupling assembly of claim 1, further comprising:
a support ring;
wherein the locking ring is in contact with an entire circumference of the lock surface of the channel and the support ring is located in the channel and in contact with the locking ring.

16. The coupling assembly of claim 1, wherein an entire exterior perimeter of the locking ring, in cross-section through the entire exterior perimeter of the locking ring, is circular formed by a circle diameter.

17. A two-piece ostomy appliance provided as a wafer attachable to a user and an ostomy bag attachable to the wafer, the two-piece ostomy appliance comprising:
a first coupling member connected to the ostomy bag and forming an aperture, the first coupling member including a first flange and a second flange spaced apart from the first flange by a channel, where the channel has a release surface and a lock surface, with the lock surface closer to the aperture than the release surface is to the aperture;
a second coupling member connected to the wafer and including a locking part having an inner wall that is sized for placement around a stoma of the user and an outer wall, a wafer flange connected to and extending from the outer wall, with the wafer flange connected to the wafer, and a locking cam formed on the outer wall of the locking part;
a ring permanently located in the channel of the first coupling member, where the ring has a first end portion and a second end portion; and
a tab connected to ends of the first end portion and the second end portion of the ring, the tab configured to move the ring reversibly between the lock surface and the release surface; and
wherein, when the ring is engaged with the lock surface, the first end portion crosses over and extends circumferentially beyond the second end portion, the second end portion engages with the lock surface such that the ring is in contact with an entire circumference of the channel, the locking cam of the second coupling member is engaged with the first coupling member to prevent uncoupling of the first coupling member from the second coupling member; wherein the tab connects to the first end portion as it extends circumferentially beyond the second end portion; and the tab is configured to move the first end portion between the lock surface and the release surface.

18. The two-piece ostomy appliance of claim 17, wherein the lock surface is closer to the second flange than the release surface is to the second flange.

19. A coupling assembly for an ostomy appliance, the coupling assembly comprising:
a first coupling member including a first flange that is attachable to an ostomy bag of the ostomy appliance, a second flange spaced apart from the first flange by a channel, and a lock surface located in the channel between the first flange and the second flange, the lock surface facing radially outward from an inner periphery of the coupling assembly;
a second coupling member including an attachment part, a wafer flange connected to the attachment part and configured to be attached to a wafer of the ostomy appliance, and a locking cam connected to the attachment part; and
a locking ring;
wherein the coupling assembly is configurable between:
a coupled state, wherein at least a portion of the locking ring engages with the lock surface around an entire circumference of the first coupling member, sections of the portion of the locking ring cross over each other within the channel, and the locking cam of the second coupling member engages with the first coupling member to prevent uncoupling of the first coupling member from the second coupling member, and
an uncoupled state, wherein the portion of the locking ring does not engage with the lock surface around the entire circumference of the lock surface and the locking cam of the second coupling member is disengaged from the first coupling member to allow the first coupling member to be uncoupled from the second coupling member.

20. The coupling assembly of claim 19, further comprising:
a locking element connected to the locking ring, where the locking element s configured to maintain engagement of the locking ring with the lock surface.

* * * * *